United States Patent
Moia et al.

(10) Patent No.: US 9,554,967 B2
(45) Date of Patent: Jan. 31, 2017

(54) ADAPTER AND DRUG CARTRIDGE ALIGNMENT DEVICE

(71) Applicant: Roche Diagnostics International AG, Rotkreuz (CH)

(72) Inventors: Franco Moia, Frenkendorf (CH); Pius Kuster, Zollikerberg (CH); Torsten Kraft, Mannheim (DE); Christoph Walther, Derendingen (CH)

(73) Assignee: ROCHE DIAGNOSTICS INTERNATIONAL AG, Rotkreuz (CH)

( * ) Notice: Subject to any disclaimer, the term of this patent is extended or adjusted under 35 U.S.C. 154(b) by 397 days.

(21) Appl. No.: 14/034,516

(22) Filed: Sep. 23, 2013

(65) Prior Publication Data

US 2014/0083517 A1  Mar. 27, 2014

(30) Foreign Application Priority Data

Sep. 27, 2012 (EP) ..................................... 12186324

(51) Int. Cl.
*A61J 1/14* (2006.01)
*A61J 1/20* (2006.01)
*A61M 39/10* (2006.01)

(52) U.S. Cl.
CPC .............. *A61J 1/1406* (2013.01); *A61J 1/1412* (2013.01); *A61J 1/20* (2013.01); *A61M 39/10* (2013.01);
(Continued)

(58) Field of Classification Search
CPC ...... A61J 1/2065; A61J 1/2089; A61J 1/1406; A61J 1/1412; A61M 39/10
(Continued)

(56) References Cited

U.S. PATENT DOCUMENTS 4,834,149 A * 5/1989 Fournier ............... A61J 1/2089
141/1
4,834,152 A * 5/1989 Howson ............... A61J 1/2089
141/27
(Continued)

FOREIGN PATENT DOCUMENTS

EP  1732624 B1  10/2008
EP  2054008 B1  1/2012
(Continued)

*Primary Examiner* — Timothy L Maust
(74) *Attorney, Agent, or Firm* — Woodard Emhardt Moriarty McNett and Henry LLP

(57) ABSTRACT

An alignment device for coupling a liquid drug cartridge with a longitudinal cartridge axis and a constricted neck portion with a cap and a piercable septum distal from the neck portion with an adapter is presented. The septum is perpendicular to the cartridge axis. The device comprises an adapter cannula with a longitudinal cannula axis to pierce the septum and a proximal cartridge engagement structure for axial aligned engagement with a distal end section of cartridge body. The device further comprises a distal adapter engagement structure for axial aligned engagement with the adapter. A coupling of the cartridge with the adapter is enabled via the alignment device. The adapter and the cartridge are, during the coupling, aligned by the cartridge engagement structure and the adapter engagement structure, respectively relative to each other such that the longitudinal cartridge axis and the longitudinal cannula axis form a common longitudinal axis.

16 Claims, 9 Drawing Sheets

(52) U.S. Cl.
CPC .... *F04C 2270/041* (2013.01); *Y10T 137/0402* (2015.04); *Y10T 137/598* (2015.04)

(58) Field of Classification Search
USPC .......................................... 141/27, 319, 329
See application file for complete search history.

(56) References Cited

U.S. PATENT DOCUMENTS

| | | | | |
|---|---|---|---|---|
| 4,936,841 A * | 6/1990 | Aoki | ...................... | A61J 1/2089 |
| | | | | 206/222 |
| 5,342,346 A * | 8/1994 | Honda | .................. | A61J 1/2089 |
| | | | | 604/411 |
| 6,277,095 B1 * | 8/2001 | Kriesel | ................ | A61M 5/152 |
| | | | | 128/DIG. 12 |
| 6,681,810 B2 * | 1/2004 | Weston | ................ | A61J 1/2096 |
| | | | | 141/18 |
| 7,470,258 B2 * | 12/2008 | Barker | ................ | A61M 5/3234 |
| | | | | 604/192 |
| 8,003,967 B2 * | 8/2011 | Fago | ....................... | G21F 5/015 |
| | | | | 250/432 R |
| 8,545,476 B2 * | 10/2013 | Ariagno | ................ | A61J 1/2089 |
| | | | | 604/411 |
| 8,801,689 B2 * | 8/2014 | Moy | ..................... | A61J 1/1475 |
| | | | | 604/408 |
| 2010/0241088 A1 | 9/2010 | Ranalletta et al. | | |

FOREIGN PATENT DOCUMENTS

| | | |
|---|---|---|
| EP | 2412395 A1 | 2/2012 |
| WO | 02/05852 A1 | 1/2002 |
| WO | 02/076374 A1 | 10/2002 |
| WO | 2009/125398 A2 | 10/2009 |
| WO | 2011/131778 A1 | 10/2011 |

\* cited by examiner

-- PRIOR ART --

ADAPTER AND DRUG CARTRIDGE ALIGNMENT DEVICE

CROSS-REFERENCE TO RELATED APPLICATIONS

This application is based on and claims priority to EP 12186324.5, filed Sep. 27, 2012, which is hereby incorporated by reference.

BACKGROUND

The present disclosure generally relates to ambulatory infusion systems and, in particular, to venting devices for use in combination with drug cartridges and ambulatory infusion devices as well as alignment devices for aligning a drug cartridge and an adapter.

Ambulatory infusion devices that are designed to be carried by a patient during everyday life night and day for an extended time period are used in a number of therapies. Such devices especially form a basis for CSII (Continuous Subcutaneous Insulin Infusion), a therapy for diabetes mellitus.

Insulin is typically provided in a cylindrical drug cartridge. A piston is sealing received in an inner volume of the cartridge. For expelling drug out of the cartridge the piston is pushed forward from a proximal to a distal direction by a motor-driven plunger rod of the infusion device. Thereby, drug is expelled out of an outlet and into an infusion cannula. The infusion cannula is coupled to the outlet of the cartridge either directly or via intermediate fluidic components, such as tubing and, in some cases, a check-valve. The piston accordingly serves as movable wall of the cartridge such that its inner volume decreases as drug is expelled.

Since ambulatory infusion devices such as insulin pumps are carried continuously during everyday life, mechanical robustness and some degree of water protection or, preferably, full water tightness are required. Therefore, the housing is often hermetically sealed during operation and only has a sealed coupling to the infusion cannula. Because drug is expelled from the cartridge which itself is arranged inside the device housing during operation, the hermetic sealing would result, without compensation measures, in a continuous decrease of the inner pressure inside the device housing over time, potentially affecting the dosing precision. Therefore, vents typically are gas-permeable and hydrophobic membranes that may be made from Gore-Tex® or a similar material. The membrane ensures continuous pressure equalization between the inner volume of the device and the environment, while preventing water or other liquids from entering the device. In addition, the membrane ensures pressure equalization in case of varying barometric pressure, such as, for example, due to weather changes and/or changes in altitude.

In some current devices, the membrane is integral part of the device housing. A corresponding device is disclosed. This arrangement, however, has the drawback that the membrane is typically more and more clogged by dirt, fabric particles, and the like, over the device lifetime—typically in a range of some years. Thereby the pressure equalization is negatively affected and in some cases voided.

In alternative designs, the membrane is provided in a separate adapter that serves as closure for a drug cartridge compartment of the infusion device via, e.g., a skewed or bayonet connector and additionally includes a coupler for coupling an infusion tubing to the outlet of the drug cartridge. Providing the membrane in such an adapter is an improvement in so far as the adapter is typically designed for a considerably shorter lifetime as compared to the infusion device itself, thus reducing the clogging problem. This arrangement, however, has the disadvantage that it can not be used in systems that do not use a separate disposable adapter. In addition, the lifetime of the adapter may still be too long to prevent clogging.

A further specific problem arises when drug cartridges are used in an ambulatory infusion device that have an outlet which is, in the isolated state, sealing closed by a self-sealing septum. For use in the infusion system, the septum is pierced by a hollow adapter cannula that fluidic couples the inner volume of the cartridge to the infusion cannula. The adapter cannula is typically part of an adapter as described above.

FIG. 1 schematically shows a typical situation when connecting a drug cartridge with septum to an adapter. Cartridge 100 is typical cylindrical and has a proximal piston that is sealing and sliding arranged in glass or plastic body 105, cartridge body 195 having an open proximal end. At its distal end, cartridge body 105 has a constricted neck portion 110 with cap 115 that includes a central septum. Adapter 200 has an adapter body 205 from which adapter cannula 210 projects. An infusion tubing or coupler for infusion tubing is part of or connected to adapter 200 for coupling to an infusion cannula. Guide 215 is provided for positioning and aligning cartridge 100 and adapter 200. Typically, Guide 215 has the form of a collar or ring that projects from a proximal bottom surface of adapter 200 and may also carry an infusion device coupler for coupling, e.g., in form of a bayonet, for coupling to the infusion device housing. Typically, guide 215 has an axial dimension of some millimeters and surrounds, i.e., has an axial overlap with, cap 115, but not cartridge body 105.

Ideally, the cannula 210 pierces the septum perpendicular to the septum, such that the longitudinal cartridge axis Z is parallel to and preferably aligned with longitudinal cannula axis Z'. In practice, however, substantial misalignment may be typically present, as shown (somewhat exaggerated) in FIG. 1, resulting in undesired transverse forces on cannula 210 and the septum.

The possibility of significant misalignment is due to the fact that cartridge 100 is guided with respect to adapter 200 via cap 115 only which has a dimension along cartridge axis Z in a range of typically 2 mm to 3 mm, which is not sufficient to ensure axial guiding.

Consequently, the septum may leak either from beginning on or start leaking during the application time of the cartridge which is typically in a range of some days up to may be two weeks. Guide 215 typically has an inner diameter that is somewhat larger than the outer diameter of cap 115.

To improve the situation, it would, at least theoretically, be possible to design adapter 200 with a considerably extended axial length of guide 215, resulting in guide 215 to axial overlap cartridge body 105 by an amount in a range of, e.g., 7 mm to 10 mm. In addition, guide 215 would need to be provided with tight inner tolerance.

In this context, it has to be understood, however, that adapter 200 needs to meet a considerable number of partly contradictory constraints and is further regulatory critical since it is of direct significance for ensuring reliable infusion. Therefore, the development time and effort for an adapter and the corresponding interface structure of the infusion device are considerable. In practice, new adapter designs are based on existing ones as far as ever possible, with as little and preferably no modification at all to the cartridge interface. In addition, a variety of drug cartridges exists which are typically provided by different suppliers than infusion pumps and adapters. In view of the generally complex and critical adapter design, providing different adapters that ensure appropriate cartridge guiding for a variety of existing and newly developed cartridges is practically unfeasible. As a consequence, the whole ambulatory infusion system is typically designed for use with a single type of drug cartridge only.

Therefore, there is a need to provide devices that improve the situation with respect to the above-identified problems, i.e. with respect to venting and/or cartridge alignment.

SUMMARY

According to the present disclosure, an alignment device and method for coupling a liquid drug cartridge having an cartridge body extending along a longitudinal cartridge axis (Z) and, at its distal end, a constricted neck portion and a cap with a piercable septum perpendicular to the cartridge axis (Z) and distal from the neck portion; and an adapter comprising an adapter cannula with a longitudinal cannula axis (Z') to pierce the septum and an infusion device coupler to mechanically couple to and engage with a housing of an ambulatory infusion device is presented. The alignment device can comprise a proximal cartridge engagement structure designed for axial aligned engagement with a distal end section of cartridge body and a distal adapter engagement structure designed for axial aligned engagement with the adapter enabling a coupling of the cartridge with the adapter via the alignment device. The adapter and the cartridge are, during the coupling, aligned by the cartridge engagement structure and the adapter engagement structure respectively relative to each other such that the longitudinal cartridge axis (Z) and the longitudinal cannula axis (Z') form a common longitudinal axis.

In accordance with one embodiment of the present disclosure, a cartridge kit is presented. The cartridge kit comprises an alignment device.

In accordance with another embodiment of the present disclosure, an adapter kit is presented. The adapter kit comprises an alignment device.

In accordance with yet another embodiment of the present disclosure, a liquid drug cartridge for use in an ambulatory infusion device is presented. The cartridge comprises a cartridge body extending along a longitudinal cartridge axis (Z), a distal end section comprising a self-sealing, piercable septum perpendicular to the cartridge axis (Z), and a number of alignment members distributed about an outer circumference of the cartridge body and extending along the longitudinal cartridge axis (Z).

Accordingly, it is a feature of the embodiments of the present disclosure to provide devices to improve venting and/or cartridge alignment. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
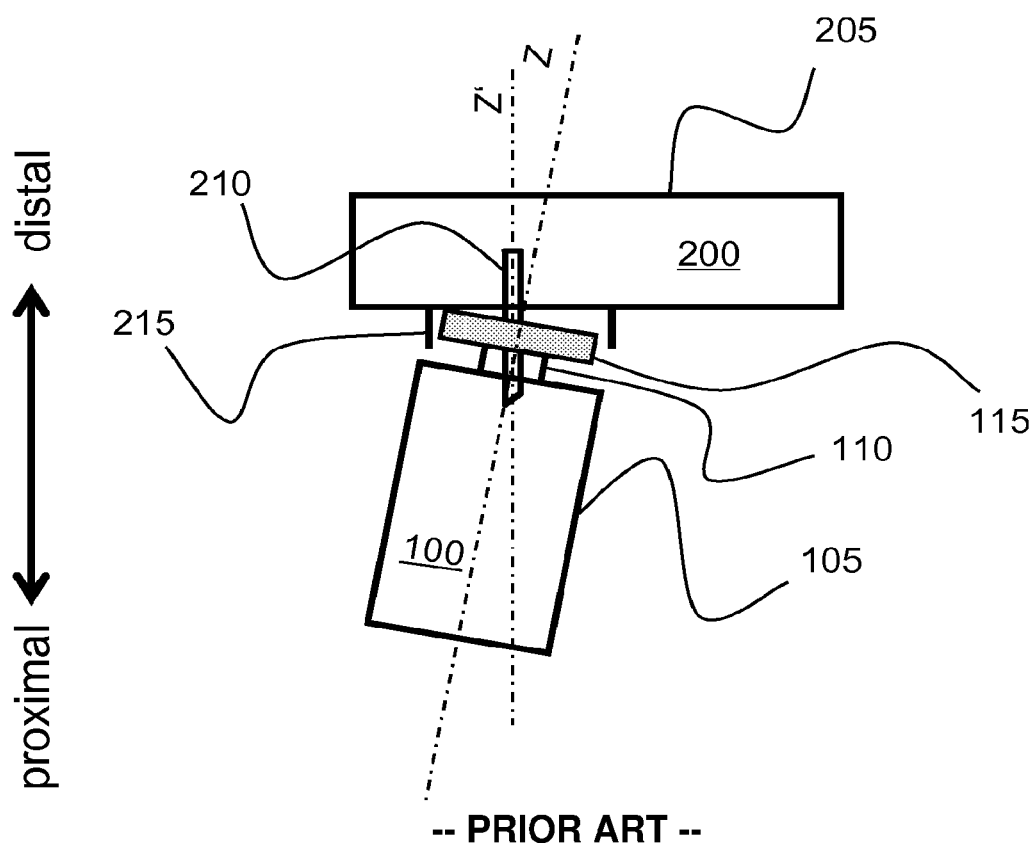
FIG. 1 illustrates a cartridge coupled to an adapter in a misaligned way according to the prior art.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A venting device comprising a venting member made from a hydrophobic and gas-permeable material is presented. The venting member can have an environment coupling surface and an opposed cartridge coupling surface enabling gas transfer and disabling liquid transfer across the venting member between the environment coupling surface and the cartridge coupling surface. The venting device can further comprise a carrier member structurally supporting the venting member.

The carrier member can be assembled to a cartridge. The cartridge can store a liquid drug in an inner volume and can have a movable wall. The movable wall can decreases the inner volume upon the stored liquid drug amount decreasing.

The venting device can be designed such that the venting device and the cartridge can form, in the assembled state, a compact common cartridge assembly. After inserting this cartridge assembly into a cartridge compartment of an ambulatory infusion device, the cartridge coupling surface fluidic can couple to a non-liquid contacting outer surface of the movable wall. At the same time, the environment coupling surface fluidic can couple to the environment.

The venting member can be attached to the cartridge and can be inserted into the cartridge compartment together with the cartridge as common cartridge assembly, rather than being integrated into the housing of the ambulatory infusion device or into an external adapter. This design can increase the flexibility with respect to the adapter design and can further ensure that the venting member is replaced each time together with the cartridge, while the adapter may have a longer lifetime.

By fluidic coupling the movable wall, via the venting member, to the environment, it can be ensured that no undesired force, resulting from an overpressure or underpressure inside the cartridge compartment can act on the liquid drug inside the cartridge via the movable wall.

The cartridge may be a cylindrical cartridge with a cartridge body that can, for example, be made from glass or plastic and can have an open proximal end.

A piston that can be typically made from plastic and/or rubber can be sealing and sliding arranged in the cartridge body and can serve as movable wall, thus resulting in a syringe-like design. The movable wall can ensure that the liquid storing volume that can be limited by an inner surface of the cartridge body and a distal inner surface of the piston can always be filled with liquid drug while no, or only a negligible amount, of air or gas may be present. This type of cartridge is typical for current devices and generally assumed in the following, if not explicitly expressed. Alternatively, however, other cartridge designs may be used. The cartridge may, for example, be made from one or more foil or membrane sheets and can be realized as fully flexible bag or pouch, or it may be semi-flexible with a rigid shell that can be covered by a foil or membrane sheet. In those embodiments, the foil or membrane sheets can serve as movable wall. In the context of CSII, typical maximum filling volumes of the cartridge may be in a range of, for example, about 1 ml to about 4 ml, such as, for example about 1.5 ml or about 3 ml.

The cartridge compartment of the ambulatory infusion device can typically have a size and shape that can fit to the cartridge. For a typical elongated cylindrical cartridge, the cartridge compartment can typically have a cylindrical or rectangular shape, such that the cartridge can fit into the cartridge compartment with some but no extensive lateral play. Typically, a plunger rod of a drive unit can project into the cartridge compartment for engaging and displacing the cartridge piston. The inner dimensions of the cartridge body, such as the inner diameter in case of a cylindrical cartridge, can accordingly be such that a distal section of the plunger rod can be inserted into the proximal section of the cartridge body via its open proximal end.

The cartridge compartment can have a fluidic tight seal against some parts and components of the infusion device, such as power supplies, drive unit components such as motors or gears, end control circuitry. The cartridge compartment may or may not be air or gas tight sealed against remaining parts of the device.

Fluidic coupling between the cartridge coupling surface of the venting member and the movable wall can be achieved via the inner volume of the cartridge compartment. Both the outer surface of the movable wall and the cartridge contacting surface of the venting member can be in fluidic communication via remaining air that may be present in the cartridge compartment when the cartridge assembly is inserted, especially in form of a "gap" between cartridge body and cartridge compartment walls. A direct physical contact between movable wall and cartridge coupling surface may not be required as long as fluidic coupling for free air exchange and pressure equalization is given.

The venting member may typically be made from Gore-Tex® or a comparable material. In some typical embodiments, the venting member can be a membrane having lateral dimensions that can be large as compared to a membrane thickness. Due to the small thickness, the gas transfer properties of a thin membrane can be particularly favorably. Alternatively, however, the venting member may have other shapes and be, for example, a small cylinder. A typical cross-sectional area of the venting member, i.e. the surface area of the environment contacting surface and the cartridge coupling surface, can be in the $mm^2$-range. In one embodiment, the venting member can be embedded in the carrier member such that the carrier member can fully surround the venting member. The venting member may be assembled to the carrier member using techniques such as adhesive bonding, ultrasonic bonding, or force fitting.

In some embodiments, the environment coupling surface and the cartridge coupling surface can have a common normal axis being, in the assembled state, parallel to a longitudinal cartridge axis. This type of arrangement can allow a particularly compact design.

In some embodiments, the carrier member can comprise an elongated coupling channel. The coupling channel fluidic can couple the environment coupling surface or the cartridge coupling surface with a peripheral surface of the venting device. This can allow an arrangement of the venting member, especially a membrane-like venting member, directly at, or close to an outer surface of the carrier member, which can be favorable with respect to assembly. While direct coupling can typically be achieved for one of the surfaces, the other of the surfaces can be fluidic coupled via the channel in the carrier member. Alternatively, however, both surfaces may be fluidic coupled via corresponding coupling channels.

In some embodiments, the carrier member can surround, in the assembled state, at least a portion of a circumference of the cartridge.

In some embodiments, the carrier member can form a cap. The cap can be put over a distal end section of the cartridge. This embodiment may be realized in a number of ways. Some typical cartridges, like the cartridge that is shown in FIG. 1, can have an elongated cartridge body that can be made from glass or plastic and can have, at its distal end, a metal cap that can be attached to the cartridge body via crimping or the like. The cap can have a cut-out that can enable access to a septum. For this type of cartridge, the cap may simultaneously serve as carrier member and the venting member may be directly integrated into a peripheral area of the cap, outside the cartridge body. For this type of design, the venting device can be an integral part of the readily assembled cartridge and can be provided to the user in this way. Alternatively, the carrier member may be realized as plastic cap that can be put over the proximal end section either during cartridge manufacture or later on, such as, for example, by a patient himself immediately prior to use. While the former design may be typically applied for cartridges that are especially designed for use in an ambulatory infusion device, the latter design may also be applied where standard cartridges, that are, for example, mainly designed for use in a pen-type injection device (so-called injection pen) where venting may not be required, are used.

Generally, the carrier member may be designed for assembly to the cartridge, in particular to a cartridge body, by a number of techniques. Assembly may especially be carried out via at least one of snap-fit, force fit, or crimping. In embodiments of the cartridge assembly that are especially designed for use in an ambulatory infusion device, the carrier may also be part of a cap as described above or may be directly integral with the cartridge body that can be, for example, made from plastic.

In some embodiments, the venting device can comprise an alignment structure. In such embodiments, the venting device can couple to a cartridge with an elongated cartridge body that can extend along a longitudinal cartridge axis and can have, at its distal end, a constricted neck portion. The cartridge can further comprise a cap with a piercable septum distal from the neck portion. The septum can be perpendicular to the cartridge axis. This type of cartridge can correspond to the example of FIG. 1.

This type of venting device can couple to an adapter. The adapter can comprise an adapter cannula with a longitudinal cannula axis to pierce the septum and an infusion device coupler to mechanically couple to and engage with a housing of an ambulatory infusion device.

This type of venting device can comprise a proximal cartridge engagement structure. The cartridge engagement structure can be designed for axial aligned engagement with a distal end section of the cartridge body and a distal adapter engagement structure. The adapter engagement structure can be designed for axial aligned engagement with the adapter, thus enabling a coupling of the cartridge with the adapter via the venting device. The adapter and the cartridge can be, during the coupling, aligned by the cartridge engagement structure and the adapter engagement structure, respectively relative to each other such that the longitudinal cartridge axis and the longitudinal cannula axis can form a common longitudinal axis.

A cartridge assembly for use in an ambulatory infusion device is presented. The cartridge assembly can comprise a cartridge and a venting. Such a cartridge assembly may be assembled by a supplier directly during production or it may be assembled by the user. The term "cartridge assembly" can comprise embodiments where the venting device can be an integral part of the cartridge as well as embodiments where the venting device can be a separate device. The cartridge assembly can fit into the cartridge compartment of an ambulatory infusion device.

In some embodiments of a cartridge assembly, the venting device can be at a distal end section of the cartridge. The distal end section can comprise an outlet for connecting to an infusion cannula.

In some embodiments of a cartridge assembly, the outlet can comprise a self-sealing, piercable septum. The cartridge of such an embodiment may, for example, be a so-called pen-type cartridge that can be typically used in co-combination with a hand-held pen-shape injection device. However, those cartridges may also be used in correspondingly designed ambulatory infusion systems, in which case a venting device can be particularly favorable. Closing the cartridge outlet by a piercable septum can be favorable in so far as septa can be self-sealing, i.e., do not require further closure, can be easily pierced by a cannula and can provide a sterile barrier. Alternatively, however, the outlet may also be designed as standard Luer coupler, as bayonet, or the like.

In some embodiments of a cartridge assembly, the cartridge further can comprise a piston and an elongated cartridge body having an longitudinal cartridge axis. The piston can be sealing arranged inside the cartridge body and can be displaceable along the longitudinal cartridge axis. The piston can have a liquid-contacting distal end and a non-liquid contacting proximal end. The cartridge contact surface can fluidic couple to the proximal end.

In some embodiments of such a cartridge assembly, the venting device can be at a proximal end section of the cartridge, such that the cartridge contact surface can be adjacent to a proximal piston front surface and the venting device can tightly cover an open proximal end of the cartridge body. In such a design, the carrier may, for example, be formed by a cap that can be put over the proximal end section of the cartridge body, or by, for example, a cap-like or disk-shaped, fit-in piece that can tightly fit into the proximal opening of the cartridge body, proximal of the piston. In a further alternative, the cartridge body itself can serve as carrier member and the venting member, typically in form of a membrane, can be directly bonded to the proximal end section of the cartridge body, for example, via adhesive bonding.

For this embodiment, the venting device can be used for ensuring pressure equalization prior to application during storage.

This embodiment can be especially useful where an ambulatory infusion device is provided pre-assembled with a cartridge being already built in. Here, the whole device can typically be designed for a single application. This may be the case for disposable single-use insulin pumps, as well as in other clinical therapies. The storage time after assembly and prior to use may be up to several years. During this time period, the device, including the cartridge, may experience considerable air pressure variations and may also be carried to significantly different heights above sea level. This may result in undesired over- or underpressure inside the cartridge, and potentially even undesired piston movement. In addition, the cartridge may need to be maintained sterile during this whole storage time.

This can be enabled by a cartridge assembly since the venting member additionally can serve as sterile barrier. In this way, providing and maintaining the whole device in a sterile state during the whole storage period can be avoided. A housing of the ambulatory infusion device can comprise a venting channel that can couple the environment coupling surface of the venting device with the environment.

In this embodiment, since the venting member can be between the piston and the typically present plunger rod that can engage the piston during application, access to the piston can need to be established at the beginning of the application. The venting member may therefore be designed to be ruptured by a plunger rod of an ambulatory infusion device. This may be achieved by the strength of the venting member that cannot withstand the force that can be applied by the drive rod when moving in distal direction from an initial retracted position in distal direction towards the piston. The rupture may be optionally supported by a perforation of the venting member. Alternatively, the venting device may be designed to be pushed forward into the cartridge body and can be permanently arranged between plunger rod and piston. In a further alternative, the venting device may flip away, for example, via a hinge, or be removed by a device user, for example, by a strap that is attached to or part of the venting device and projects out of the infusion device housing.

An adapter for coupling a cartridge assembly with an infusion cannula and an ambulatory infusion device is presented. The adapter can comprise an infusion device coupler to mechanically couple to and engage with a housing of the ambulatory infusion device, a drug channel to fluidic couple the inner volume of the cartridge with an infusion cannula, and a venting channel for establishing, in the assembled state, a fluidic tight coupling of the environment and the environment contacting surface and the environment via the venting channel.

For a cartridge assembly in which the cartridge and the venting assembly can form a compact common unit, the cartridge assembly can be inserted into the cartridge assembly as a whole. Some closures can be therefore required for establishing a fluidic coupling between environment coupling surface and environment. For this purpose, the venting channel can be provided in an adapter. The fluid-tight connection may be realized by O-ring seals that can be part of the adapter or the venting device, or sealing elements that can be structural part of an adapter body or the carrier member, for example, via providing a soft sealing member in a multi-component injection moulding process. An adapter-cartridge-unit can comprise a cartridge assembly and an adapter.

An ambulatory infusion device can comprise a cartridge assembly with a venting device. The venting member can be designed to be ruptured by a plunger rod of the ambulatory infusion device. The ambulatory infusion device can further comprise a drive unit with a linearly displaceable plunger rod. The plunger rod can be designed to rupture the venting member and to subsequently engage the distal piston end. The ambulatory infusion device can further comprise a venting channel. The venting channel can fluidic couple the environment coupling surface with the environment.

An alignment device can be presented. The alignment device can be designed for coupling a liquid drug cartridge with an adapter via the alignment device. The cartridge can be a cartridge as discussed and shown in FIG. 1. In particular, the cartridge can have an elongated cartridge body that can extend along a longitudinal cartridge axis and can have, at its distal end, a constricted neck portion. The cartridge can further comprise a cap with a piercable septum distal from the neck portion. The septum can be perpendicular to the cartridge axis. The adapter can comprise an adapter cannula with a longitudinal cannula axis to pierce the septum.

The alignment device can comprise a proximal cartridge engagement structure designed for axial aligned engagement with a distal end section of the cartridge body. The alignment device can further comprise a distal adapter engagement structure designed for axial aligned engagement with the adapter.

The alignment device can enable a coupling of the cartridge with the adapter. The adapter and the cartridge can be, at the end and preferably also during the coupling process, aligned by the cartridge engagement structure and the adapter engagement structure, respectively relative to each other such that the longitudinal cartridge axis and the longitudinal cannula axis can form a common longitudinal axis.

By providing an alignment device, the cartridge can be guided relative to the adapter not only along the axial height of the cap. Instead, the axial guiding length can be substantially longer without requiring modification of cartridge and/or adapter. Instead, the alignment device can be designed comparatively easily and fast to fit for a given cartridge and adapter. With the relative tolerances between cartridge and adapter being unaffected, the longer guiding length can considerably reduce the angular play and accordingly the angular misalignment.

By aligning the longitudinal cartridge axis and the longitudinal cannula axis, i.e., by ensuring the two axis to be in coincidence, septum leakage problems as discussed above with reference to FIG. 1 can be avoided or at least considerably reduced. The alignment device can exploit the fact that typically the cartridge is manufactured with high (rotational) symmetry about the longitudinal cartridge axis and with sufficiently tight tolerances. Via the disclosed alignment device, these properties of the cartridge can be used to ensure alignment with the adapter cannula.

The alignment device can enable, during the coupling process, an aligned and guided relative displacement of the cartridge and the adapter towards each other along the common longitudinal axis. During the displacement, the adapter cannula can come in contact with and can finally pierce the septum. This can ensure that correct alignment is given not only in the assembled final state, but also during the assembly process. During the coupling process, the guided and aligned engagement and coupling can start at an axial distance of cartridge and adapter where the tip of the adapter cannula can still be axial displaced from and does not pierce the septum.

In some embodiments, the cartridge engagement structure can be designed to surround, in the assembled state, a distal section of the cartridge body and/or to project, in the assembled state, from the cap in proximal direction. In this embodiment, the symmetry and tight tolerances of the cartridge body can be exploited for the alignment.

Alternatively or additionally, the cartridge engagement structure can be designed to surround, in the assembled state, at least one of the cap and the neck portion of the cartridge body. In this embodiment, the symmetry and tight tolerances of the neck portion of the cartridge body and/or the cap can be exploited for the alignment. The adapter engagement structure may especially surround, in the assembled state, the cap and at least a part of the neck portion. Here, the length of the normally "dead" neck portion can be used for guiding.

In some embodiments, the adapter engagement structure can have anti-rotation ribs designed to engage the adapter, thus preventing a relative rotation between the adapter and the alignment device in the engaged state. Thereby, it can be ensured that the adapter can be displaced towards the cartridge in a pure translational motion, i.e. without superimposed rotation, which can be favorable with respect to tightness. Favorably, the anti-rotation ribs can extend along the common longitudinal axis in the engaged state. Such anti-rotation ribs may also be present in a venting device. In some embodiments, the alignment device can be designed not to radially extend, in the assembled state, beyond the cartridge body. The term "radially" can refer to a direction perpendicular to the cartridge axis. This embodiment can have the property that the radial dimension in the assembled state can be given by the cartridge body and cannot be further increased by the alignment device. This can be favorable since the radial dimension can determine the diameter of a corresponding cartridge department of the infusion device and thus the device thickness, which can be generally desired to be as slim as possible.

In some embodiments, the alignment device can have a general tubular shape, extending along the common longitudinal axis. For such embodiments, the cartridge engagement structure can typically be formed, fully or partly, by the inner surface of a proximal tube section. The adapter engagement structure can typically be comprised in a distal tube section and may be designed in various ways.

For some tubular designs of an alignment device, the alignment device can comprise a proximal tubular member and a distal tubular member. The proximal tubular member can form the cartridge engagement structure. The distal tubular member can form or comprise the adapter engagement structure. The proximal tubular member and the distal tubular member can be displaceable with respect to each other in guided way along a common tube axis. In the assembled state, the common tube axis can correspond to the common longitudinal cartridge axis and longitudinal cannula axis. Such a telescopic design can be particularly compact.

In some embodiments of an alignment device, the alignment device can comprise a cartridge block designed to prevent further relative displacement between the alignment device and the cartridge upon the cartridge block hitting the cartridge. Such a cartridge block may also be present in a venting device.

In some tubular designs that comprise a cartridge block. The cartridge block can comprise at least one projection member. The at least projection member can project radial into an inner volume of the tube. The projection member may, for example, have a dent-shape or be designed as rim or protrusion. Alternatively or additionally, a cartridge block of the alignment device may comprise a proximal front surface of the tube. Further displacement can be prevented upon the front surface the cartridge body.

In some embodiments of the alignment device, the cartridge engagement structure and the adapter engagement structure can overlap in axial direction. As will be discussed below, such an overlap can be favourable with respect to compactness in the connected state.

In some embodiments, the adapter engagement structure can comprise at least one of a distal section of an outer circumferential surface of the alignment device, an inner circumferential surface of a distal section of the alignment device, and an alignment cavity. The alignment cavity can be formed in a distal front surface of the alignment device.

In some embodiments of an alignment device, the alignment device can further comprise a venting member made from a hydrophobic and gas-permeable material. The venting member can have an environment coupling surface and an opposed cartridge coupling surface enabling gas transfer and disabling liquid transfer across the venting member between the environment coupling surface and the cartridge coupling surface. This type of alignment device can be designed such that, when coupled the cartridge, the cartridge can have a movable wall. The cartridge coupling surface can fluidic couple to a no-liquid contacting outer surface of the movable wall and the environment coupling surface can fluidic couple to the environment. Such an embodiment can combine the advantages of a venting device and an alignment device in a common, compact unit.

A cartridge kit can comprise an alignment device and a liquid drug cartridge as discussed above, with the cartridge and the alignment device being coupled or designed to couple via the cartridge engagement structure of the alignment device.

An adapter kit can comprise an alignment device and an adapter as discussed above, with the adapter and the alignment device being coupled or designed to couple via the adapter engagement structure of the alignment device. Both a cartridge kit and an adapter kit can be favorably supplied to a user in a disposable packing, either readily pre-assembled or in separate pieces.

A method for coupling a cartridge as discussed above with an adapter as discussed above via an alignment device as discussed above can be presented.

A liquid drug cartridge for use in an ambulatory infusion device is presented. A cartridge can have a cartridge body extending along a longitudinal cartridge axis. The cartridge can further have a distal end section. The distal end section can comprise an a self-sealing, piercable septum perpendicular to the cartridge axis. The cartridge can further have a number of alignment members. The alignment members can be distributed about an outer circumference of the cartridge body. The alignment members can extend along the longitudinal cartridge axis. The alignment members can fulfill the same purpose as the distal adapter engagement structure of an alignment device as discussed above. The alignment members can accordingly be designed for axial aligned engagement with an adapter.

In some embodiments of cartridge including alignment members, the number of alignment members can be three or four. While three alignment members that may be equally distributed around the cartridge body with an angle of 120° between the alignment members can be sufficient for axial guiding, four equally distributed alignment members with an angle of 90° between them can be considered preferable with respect to symmetry and injection moulding production processes.

While a separate alignment device can be favourable for use in combination with already designed or existing cartridges, such as pen-injector type cartridges, the present cartridge design can considered be favorable for newly designed cartridges.

Figure 2A:
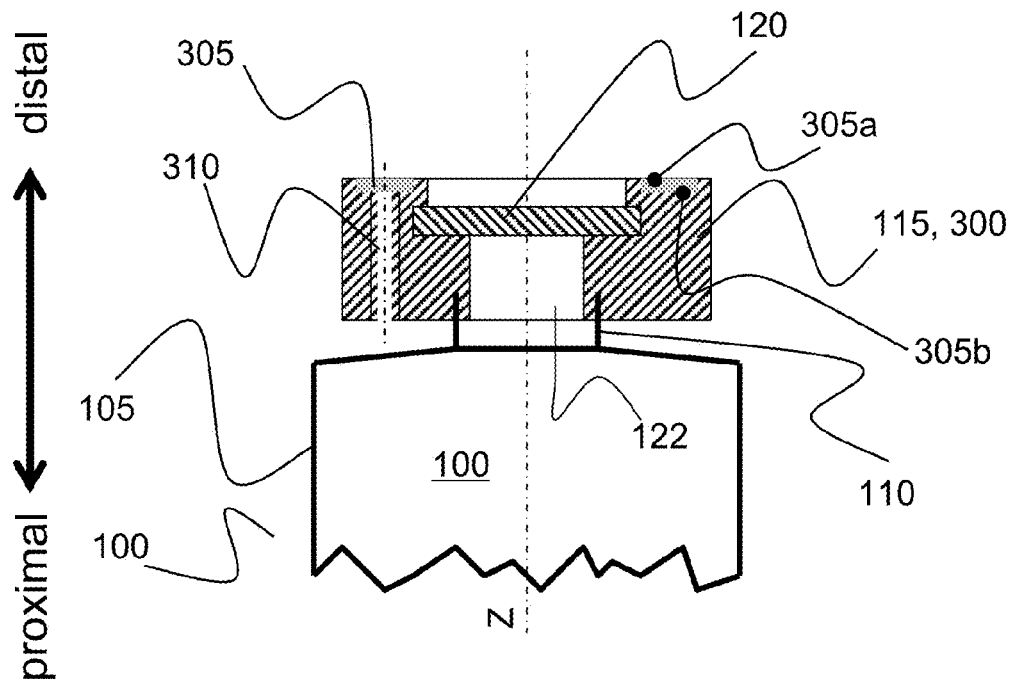
FIGS. 2a-b illustrate schematically a venting device according to an embodiment of the present disclosure.
Figure 2B:
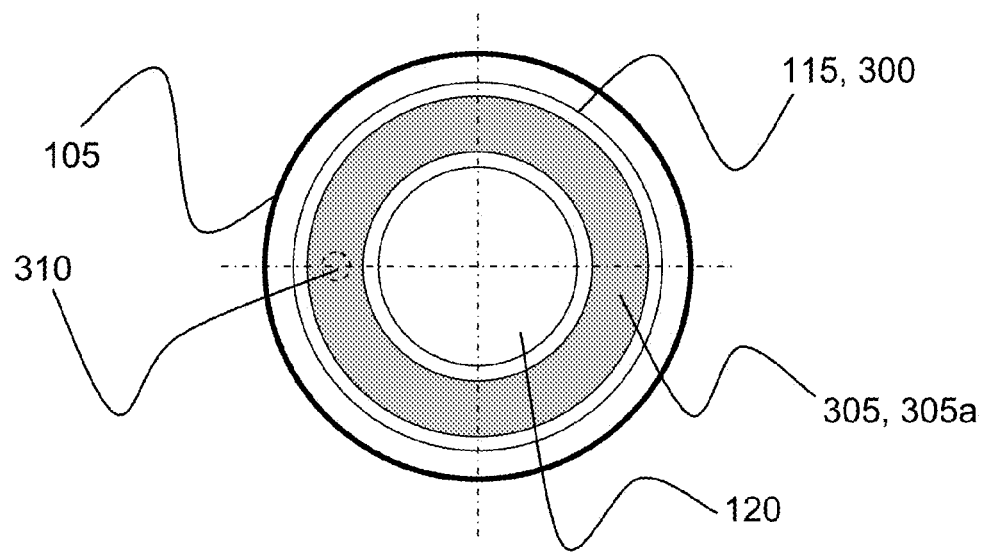

Referring initially to FIGS. 2a-b, FIG. 2a schematically shows a distal top section of a liquid drug cartridge 100 with a venting device 300 included in a cap 115 of the cartridge 100 in a cross-sectional view. FIG. 2b shows a corresponding top view. Cartridge 100 can exemplarily be shown as having a cylindrical cartridge body 105 that can typically be made from medical-grade glass or plastic. Cartridge body 105 can have a constricted neck portion 110 (referenced in FIG. 2a only). Cap 115 can typically be made from metal or plastics and sealing attached to distal end of neck portion 110 via pressing or crimping. A self-sealing and piercable septum 120 can be sealing arranged in cap 115. To this extent, cartridge 100 can be a standard drug cartridge as it is typically used in pen-like injection devices (injection pens) and some ambulatory infusion devices, with the specific design being exemplary. For example, the cartridge body 105 may have a non-cylindrical cross section or may be formed by a fully or partly flexible pouch or bag. Instead of septum 120, the outlet may be realized differently, for example as male Luer coupler or any sort of suited proprietary fluidic coupler.

The venting device 300 can be included in cap 115, with the cap simultaneously serving as carrier member. The venting member can be formed by a hydrophobic and gas-permeable membrane 305 that can have the shape of a ring and can be arranged in a concentric circumferential recess in a distal front surface of cap 105.

While environment coupling surface 305a can be directly coupled to the environment, adjacent cartridge coupling surface 305b can be coupled with a peripheral surface of cap 115 via elongated coupling channel 310 that is exemplarily show as bore which can serve as coupling channel.

In FIGS. 2a, 2b, only a single bore 310 is shown as coupling channel, which, however may not be essential. Independent of the permeability of membrane 305, the inner device volume that may need to be vented, but also factors such as manufacturing aspects may lead to an arrangement with a different number of channels, e.g., two, three, four or six channels. The one or more coupling channels may also have a different cross section. For example, coupling channel 310 may have the shape of an elongated slot that extends about a section of the circumference.

Figure 3:
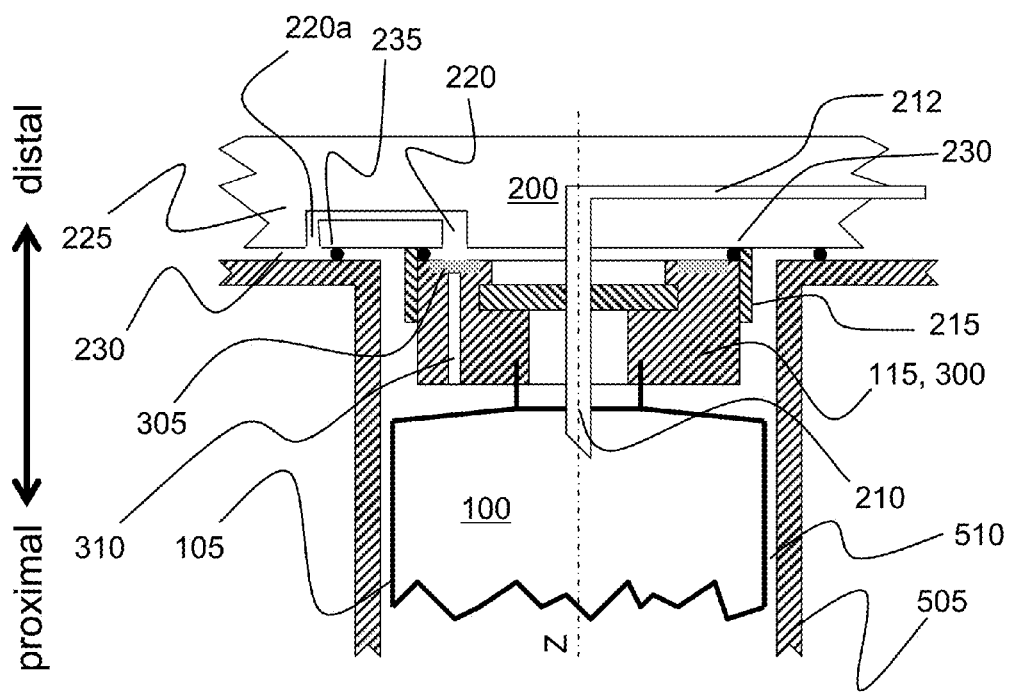
FIG. 3 illustrates schematically the venting device of FIGS. 2a-b in an assembled state, connected to a cartridge, an adapter and an ambulatory infusion device according to an embodiment of the present disclosure.

In the following, reference is additionally made to FIG. 3. FIG. 3 schematically shows the cartridge 100 with venting device 300 when inserted into cartridge compartment 510 of an ambulatory infusion device, with element 505 indicating a housing of the ambulatory infusion device, thus defining cartridge compartment 510.

After insertion of cartridge 100, cartridge compartment 510 can be at its distal end closed by adapter 200. Adapter 200 with adapter body 225 and guide 215 can be coupled to housing 505 via an infusion device coupler, for example, in form of a bayonet. An adapter cannula 210 can extend, inside the adapter 200, into a drug channel 212 for coupling to an infusion cannula.

At the connection between adapter 200 and housing 505, adapter 200 can comprise two sealing elements that are exemplarily shown as O-rings 230, 235. Inner O-ring 230 can be arranged such that it can press onto cap 115, thus axially supporting cartridge 100. Outer O-ring 235 can press onto housing 505. O-rings 230, 235 can form a fluidic sealing that can be tight with respect to both liquids, in particular insulin and water, and with respect to gas, such as, air.

Adapter 200 can comprise a through-going venting channel 220. "Through-going" can be meant in the sense that the venting channel 220 may not include elements such as valves or membranes that may need to be passed by a gas flow through venting channel 220. One end of venting channel 220 can be aligned with the environment coupling surface 305a (referenced in FIG. 2). The other end 220a of venting channel 220 can end in a gap that can exist between housing 505 and adapter body 225, thus bridging the O-ring sealings 230, 235. The gap can be part of or can be fluidic coupled to the environment.

As far as air is concerned, the inner volume of cartridge compartment 510 can be accordingly coupled to the environment via coupling channel 310, membrane 305, and venting channel 220. With respect to water, however, the inner volume of cartridge compartment 510 can be isolated from the environment because of the hydrophobic properties of membrane 305. Venting channel 220 may end at any other suited peripheral surface of adapter body 225. The end of venting channel 220 may be arranged such that free air flow can be maintained but it can be, as far as possible, protected against the intake of dirt or particles that may otherwise clog venting channel 220.

As can be seen in FIG. 3, a gap can be present in cartridge compartment 510 between the outer wall of cartridge body 105 and the surface of housing 505. Via this gap, the piston that can be located in a proximal section inside cartridge body 105, can also be coupled with the environment with respect to air, thus venting the inner volume of cartridge compartment 510.

Besides venting cartridge compartment 510, FIG. 3 shows an additional favorable property of a venting arrangement. In some cases, septum 120 can tend to leak. Besides drug delivery to the patient being interrupted or at least negatively affected in this case, many liquid drugs, such as typical liquid insulin formulations, can be corrosive. At least a portion of the drive system of the ambulatory infusion device, such as, for example, a plunger rod, can typically project into cartridge compartment 510 and may accordingly be damaged. In the shown arrangement, however, all connections between septum 120 (referenced in FIG. 2) and the inner volume of cartridge compartment 510 can be blocked for liquid by membrane 305 and O-ring sealings 230, 235. Even in case of a septum leakage, critical parts of the infusion device, in particular a plunger rod, do accordingly not come into contact with the drug.

Figure 4A:
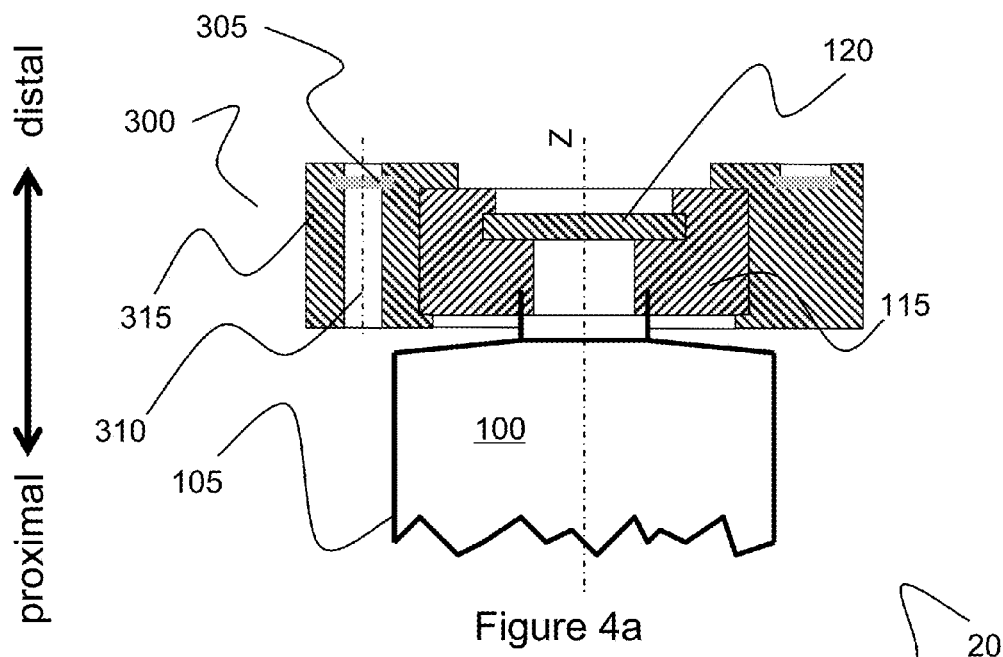
FIGS. 4a-b illustrate schematically a venting device according to another embodiment of the present disclosure.
Figure 4B:
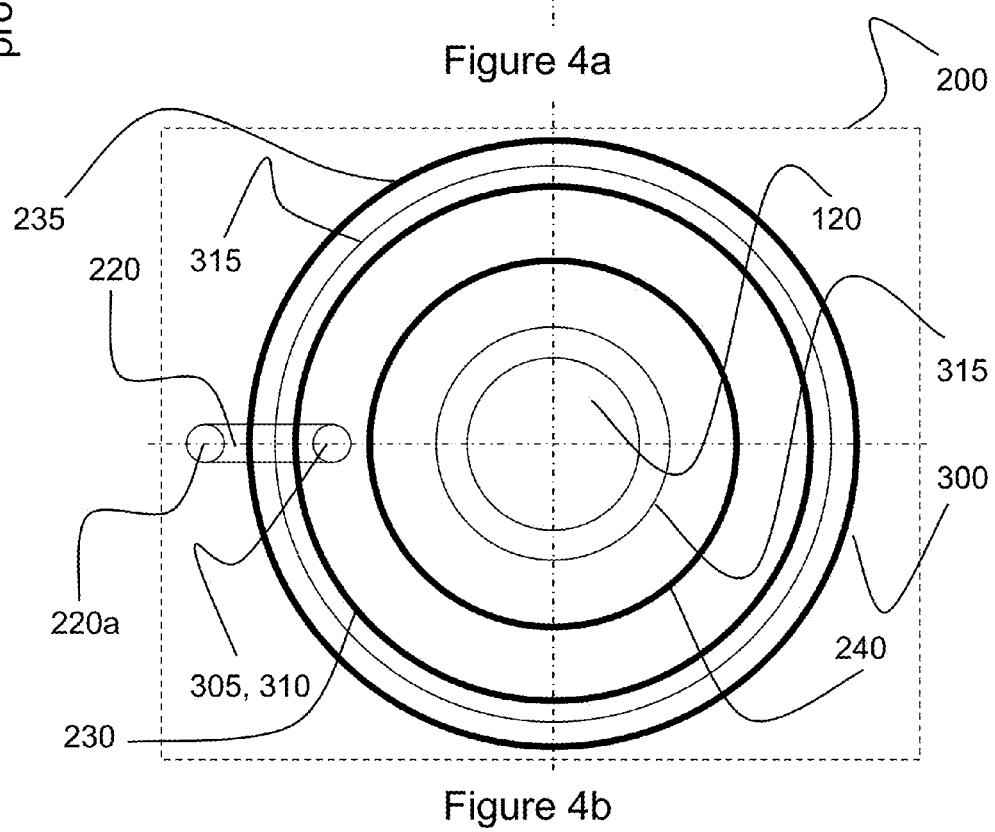

FIGS. 4a-b schematically illustrate a further embodiment of a venting device in accord accordance with the present disclosure. FIG. 4a shows venting device 300 when can be assembled to cartridge body 105.

In contrast to the above embodiment, venting device 300 cannot be included in cap 115 of cartridge 100 (visible in FIG. 4a) and accordingly cannot be integral with cap 105. Instead, carrier member 315 can be provided as dedicated component that can typically be realized as injection-molded plastic component. Membrane 305 and coupling channel 310 can be arranged in substantially the same way as they are in the above-described embodiment. Cartridge 100 and venting device 300, in combination, can form a compact cartridge assembly.

The embodiment of FIG. 4a can have the particular property that it may not require a special or modified design of the cartridge itself. Cartridge 100 (visible in FIG. 4a) may, for example, be a standard cartridge as typically used in pen-type injection devices. Carrier member 315 can be a cap that fits over cap 115 via snap fit or the like by a movement in the proximal direction relative to cartridge 100. Once assembled, venting device 300 cannot be removed without damaging venting device 300 and/or cartridge 100.

Venting device 100 may alternatively be assembled to cartridge 100 in other ways. Carrier member 315 may, for example, be a ring with a slit, thus allowing carrier member 315 to be temporarily widened to be fit over cap 115 by radial movement.

FIG. 4b schematically shows the geometric arrangement when the combination of cartridge 100 and venting device 300 is assembled with adapter 200 from a top view.

While the general design of adapter 200 can be similar to that shown in FIG. 3, the arrangement of venting channel 220 and the O-ring sealings can be slightly different. In one embodiment, three O-rings 230, 235, 240 or functionally equivalent sealing components can be present in adapter 200. The arrangement of O-rings 230, 235 can be equivalent to the description as given with reference to FIG. 3. That is, O-ring 230 can press, in the assembled state, onto carrier member 315 in axial direction, while O-ring 235 can press onto the infusion device housing. Both O-rings can be bridged by venting channel 220 with outlet 220a.

An additional innermost third O-ring 240 can also press onto carrier member 315 and can be between the septum 120 and membrane 305, thus providing a fluidic separation between the septum 120 and membrane 305. Alternatively, an arrangement with two O-rings may be used, with either of the O-rings 230, 240 omitted.

Like in the previously embodiment, septum 120 can be fluidic decoupled from the inner volume of the cartridge compartment 510 (see FIG. 3) in the assembled state, thus preventing damage in case of a septum leakage.

For a cartridge with a venting device, as shown in FIGS. 2 and 3, anti-rotation ribs may optionally be provided at the outer circumferential surface of the cap 115, the anti-rotation ribs extending in longitudinal direction. Those ribs can engage guide 215 of the adapter 200, thus preventing relative rotation during assembly, which can be advantageous with respect to tightness. In an analog way, such anti-rotation ribs may be provided at the outer circumferential face of the carrier member 305 if the venting-member is provided separately.

A number of ambulatory infusion devises can have a cartridge compartment 510 that can be loaded as shown here, by inserting drug cartridge 100 in axial direction and closing the opening by disposable adapter 200. Alternatively, however, no disposable adapter may be present and cartridge compartment 510 may be closed by a hinged door or the like that can be part of device housing 505. Since, according to the present disclosure, the venting member can be part of the cartridge assembly, venting devices in accordance with the present disclosure may be used in combination with such devices as well.

Figure 5:
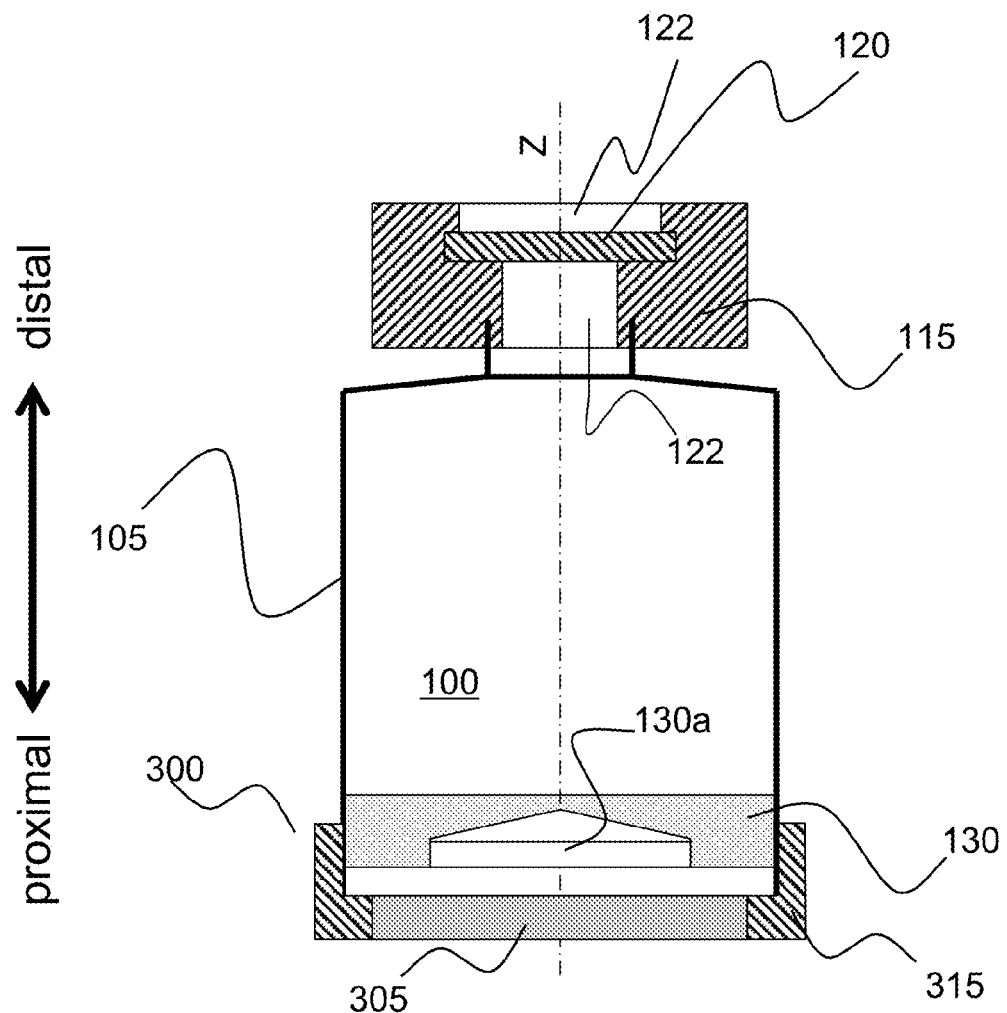
FIG. 5 illustrates schematically shows a venting device connected to a cartridge according to a further embodiment of the present disclosure.

FIG. 5 shows a further exemplary arrangement of a cartridge 100 in combination with a venting device. Besides the integrated the venting device, the design of cartridge 100 can correspond to the previously described embodiments. Therefore, the same reference numbers are used for identical or corresponding elements.

Cartridge 100 can generally be designed in the same way as in the previously embodiment, with FIG. 5 additionally showing a piston 130 that can be sealing received inside cartridge body 105 and slidable along longitudinal cartridge axis Z from proximal towards distal for expelling drug.

The venting device can be at the proximal end cartridge body 105. Carrier member 315 of the venting device can be disk-shaped cap that can tightly fit around the proximal end of cartridge body 105 which can, for example, be injection molded plastic component. Membrane 305 of the venting device can be supported and fully surrounded by carrier member 315. While membrane 305 is shown with the same thickness as carrier member 315, this may not be the case in a specific embodiment. In particular, membrane 305 may be considerably thinner.

Figure 6:
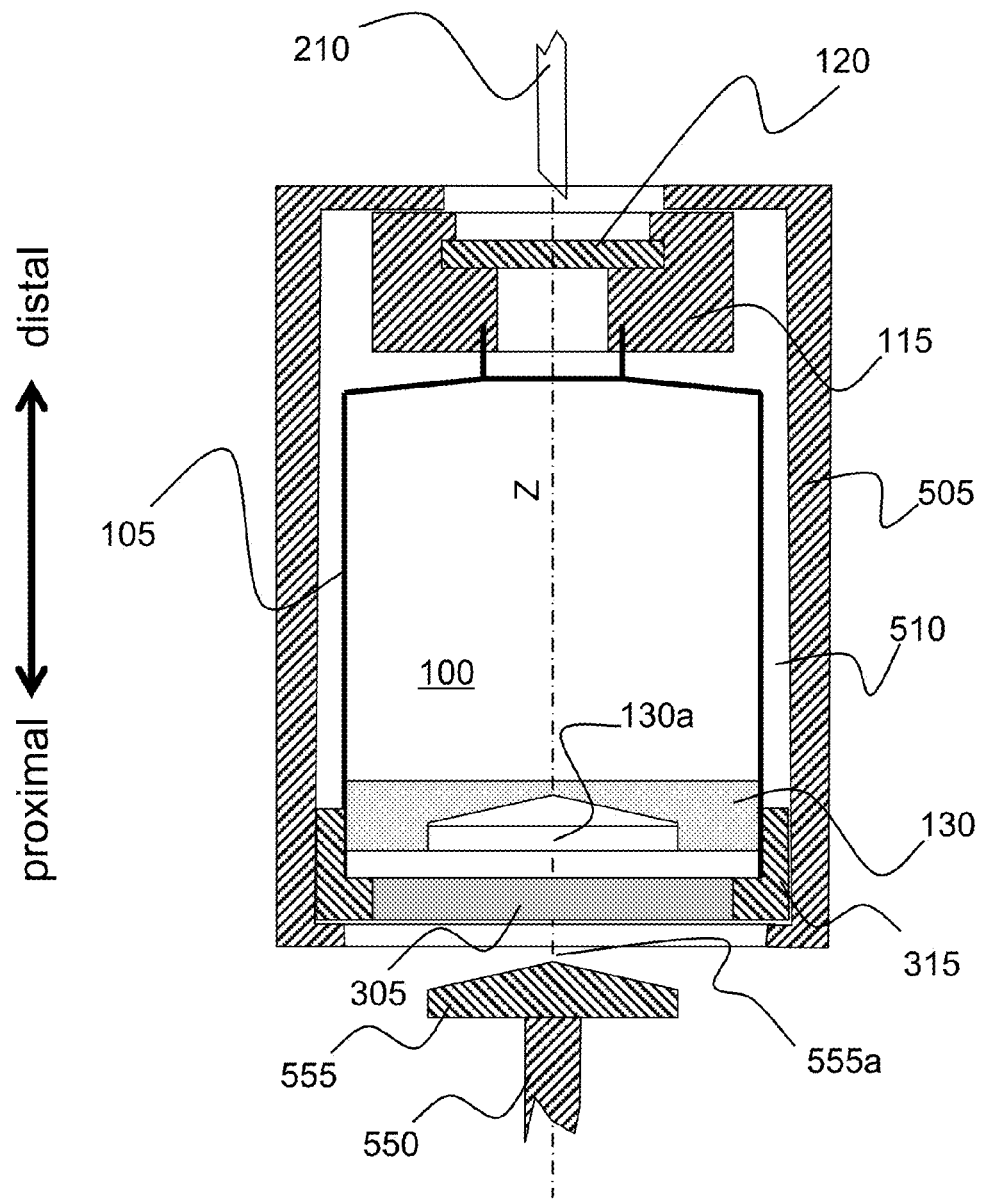
FIG. 6 illustrates schematically an ambulatory infusion device with a cartridge and venting device of FIG. 5 according to an embodiment of the present disclosure.

FIG. 6 schematically shows cartridge assembly 100, 300 of FIG. 5 when assembled into cartridge compartment 510 of an ambulatory infusion device. The cartridge compartment 510 can be formed by housing walls 505. FIG. 6 further shows cannula 210 for piercing septum 120, thus establishing fluidic access to the inner volume of cartridge 100. In an initialization phase prior to starting the infusion, piercing cannula 210 can be moved in proximal direction to pierce the septum 120. Advantageous, the ambulatory infusion device can comprise a corresponding cannula drive for this purpose. The cannula drive can be controlled via control circuitry of the ambulatory infusion device.

FIG. 6 further shows plunger rod 550 of the ambulatory infusion device that can be proximal of drug cartridge 100 and can carry, at its distal end, a pusher plate 555. Plunger rod 550 with pusher plate 555 can form part of a typically electric drive system of the ambulatory infusion device.

FIG. 6 shows plunger rod 550 in an initial, most proximal or fully retracted position. In the initialization phase, plunger rod 550 with pusher plate 555 can be moved forward in distal direction. During this process, pointed distal end 555*a* of pusher plate 555 can rupture membrane 305 and can precede its motion until pusher plate 555 is seated in the corresponding recess 130*a* of piston 130. Further advancing plunger rod 550 can result in piston 130 being pushed forward in distal direction, thus expelling liquid drug.

A number of variants and modifications are well possible. For example, the pusher plate 555 may have the shape of a cylindrical disc without pointed distal end 555*a* or may be coupled to piston 130 in a different way, for example, via a screw or snap fit. In some embodiments, recess 130*a* may not be present.

It can be seen that in the initial state as shown in FIG. 6, both septum 120 and membrane 305 can each form a sterile barrier, thus resulting in all drug-contacting elements in a sterile state. In this configuration, the ambulatory infusion device may be stored for an extended time period up to several years, with cartridge 100 filled with liquid drug and assembled into the infusion device.

Figure 7:
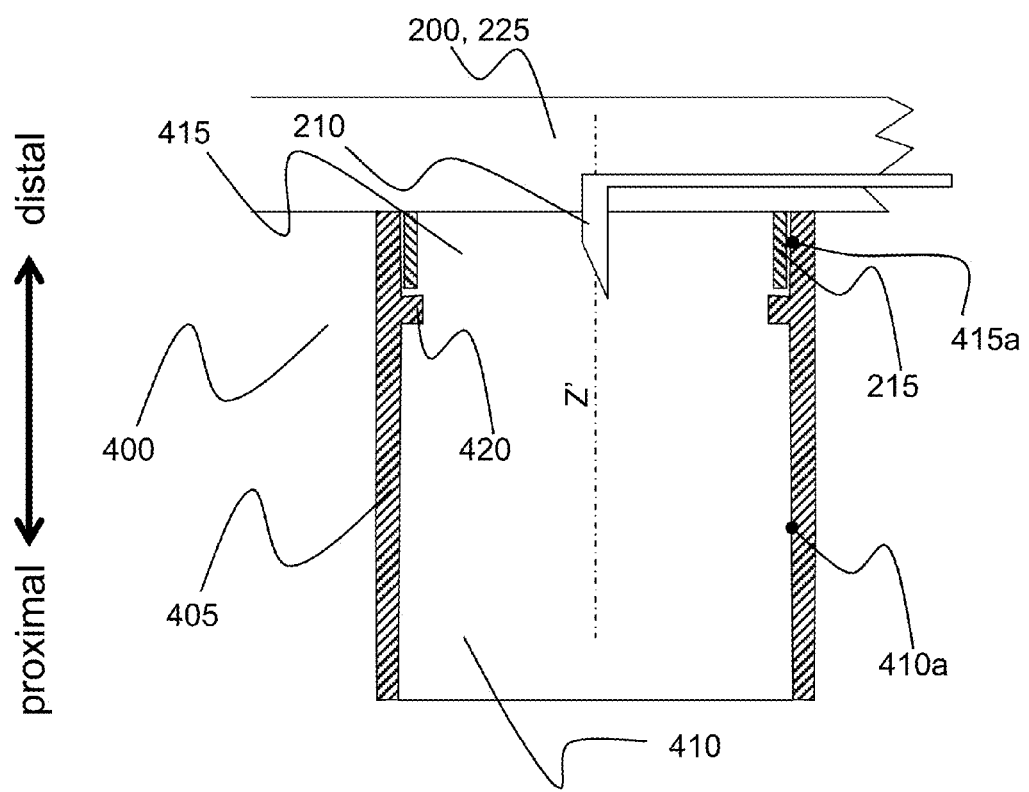
FIG. 7 illustrates schematically an alignment device according to an embodiment of the present disclosure.
Figure 8:
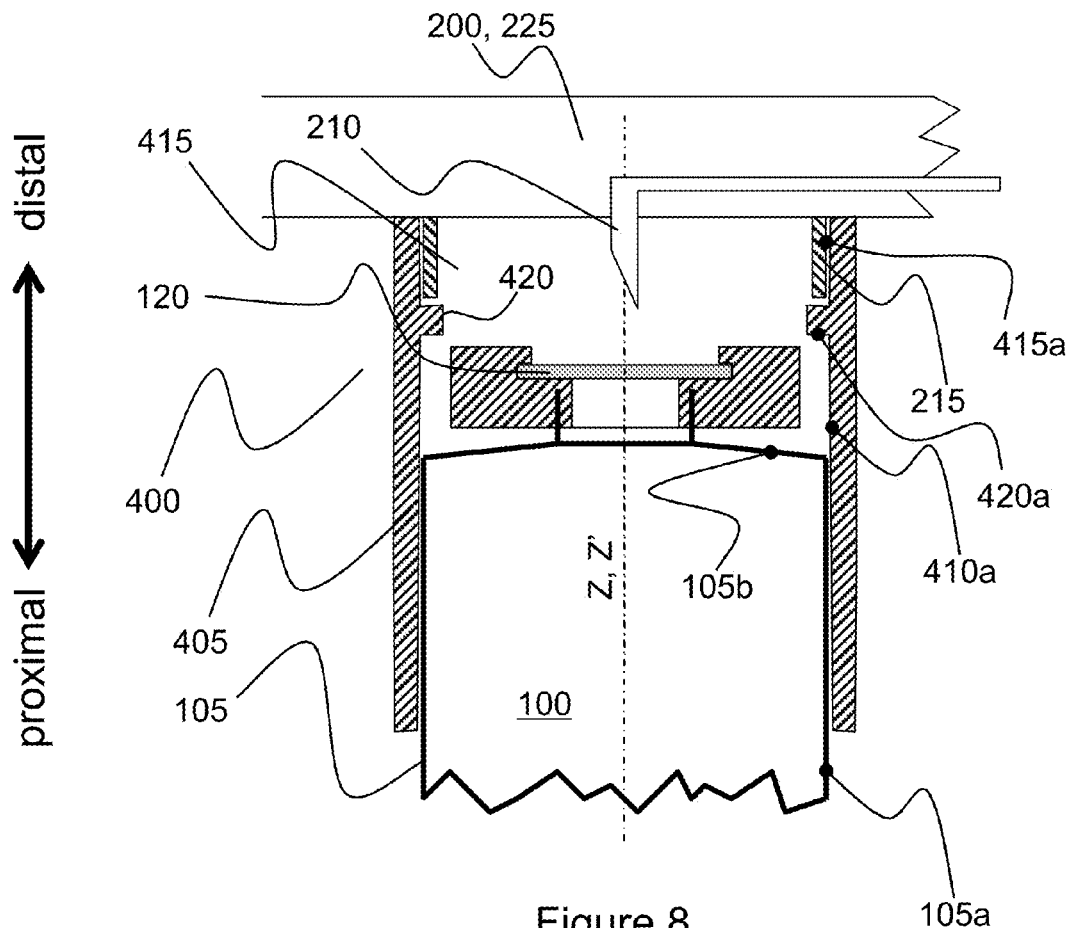
FIG. 8 illustrates schematically the alignment device of FIG. 7 coupled to an adapter and a cartridge according to an embodiment of the present disclosure.

FIG. 7 and FIG. 8 illustrate an alignment device 400. In the following description of alignment devices, adapters and cartridges that couple to the alignment device can be generally assumed to be designed in the same way as discussed before in the context of venting devices, with identical or corresponding elements having the same reference numbers.

FIG. 7 shows alignment device 400 when attached to adapter 200. The walls of guide 215 can be parallel to longitudinal cannula axis Z' of adapter cannula 210 and can perpendicularly project from an underside of adapter 200 in proximal direction. In the assembled state, guide 215 can engage and couple with the distal adapter engagement structure of the alignment device.

Alignment device 400 can have a general tubular shape with body 405. In a distal section, the inner tube diameter can correspond to the outer diameter of guide 215 such that it can fit over guide 215 smoothly and with little play. The distal tube section, and in particular its inner surface 415*a*, can accordingly form the distal adapter engagement structure 415.

In a proximal section, the inner tube diameter can correspond to the outer diameter of a drug cartridge body such that it can fit over the cartridge body smoothly and with little play. The proximal tube section, and in particular its inner surface 410*a*, can accordingly form cartridge engagement structure 410. Exemplarily, both diameters can be identical in the embodiment of FIG. 7. Between adapter engagement 415 and cartridge engagement structure 410, a ring-shaped protrusion 420 can project into tubular body 405.

FIG. 8 shows alignment device 400 readily assembled to adapter 200. Adapter 200 and alignment device 400 may be provided in this way, readily attached to each other. Alternatively, however, they can be provided separately and assembled only prior to use, e.g. by a user, such as a patient.

FIG. 8 shows the situation when coupling adapter 200 together with alignment device 400 to a drug cartridge 100. Adapter 200 can be moved, together with attached alignment device 400, in proximal direction towards cartridge 100. During this process, circumferential surface 105*a* of cartridge body 105 can be in guided, preferably smooth and substantially play-free sliding engagement with inner tubular surface 410*a* of cartridge engagement structure 410 (referenced in FIG. 7), resulting in cartridge longitudinal axis Z and cannula longitudinal axis Z' being aligned. Cartridge engagement structure 410 may not need to extend over the total length of cartridge body 105 as long as it is sufficiently long to provide a guide and prevent tilting. Typically, it can have an axial overlap with cartridge body 105 in a range of some millimeters. To ensure proper alignment when adapter cannula 210 pierces septum 120, cartridge engagement structure 410, i.e. inner circumferential surface 410*a* of tubular body 405, can be sufficiently long to ensure that the sliding contact between surface 105*a* of cartridge body 105 and inner tubular surface 410*a* can be established before the sharpened tip of adapter cannula 210 can pierce septum 120. The assembly process can be complete when proximal surface 420*a* of protrusion 420 hits distal end 105*b* of cartridge body 105, thus preventing further relative displacement. Protrusion 420 can accordingly serve as cartridge block. Other kinds of projection members, such as bumps or dents, may serve as cartridge block, too.

In a variant of this embodiment, adapter engagement 415 may be realized by the outer circumferential surface of body 405 in a distal section of body 405 rather than the inner circumferential surface.

Cartridge 100 and adapter 200 may be assembled via alignment device 400 prior to inserting cartridge 100, together with alignment device 400, into the cartridge compartment of an infusion device. Alternatively, cartridge 100 may be inserted into the cartridge compartment prior to assembling it with adapter 200 via alignment device 400. In a further variant, cartridge 100 and alignment device 400 can be assembled first and subsequently attached to adapter 200.

Figure 9:
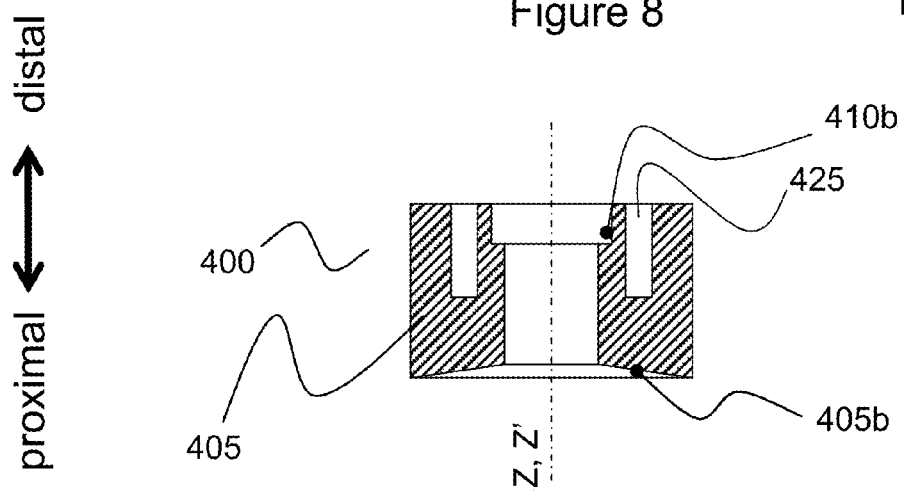
FIG. 9 illustrates schematically a further embodiment of an alignment device according to an embodiment of the present disclosure.

FIG. 9 shows a further alternative embodiment of alignment device 400. Here, the adapter engagement structure can be realized as a circumferential slot 425 in a distal front surface of device body 405. The slot 425 can be an alignment cavity. Slot 425 can be coaxial with tubular body 405 and can be designed for axial aligned engagement with the adapter, for example, a guide 215 as shown in FIG. 8, in a smooth sliding and preferably substantially play-free fit. The cartridge block can be realized by proximal front surface 405*b* of body 405 that can be shaped to fit to the distal front surface of the cartridge body. The hollow inner volume of device body 405 can receive the neck of a cartridge body in a proximal section and the cap of the cartridge in a wider distal section. Proximal front surface 405*b* and inner circumferential surface 410*b* in the distal section, can serve, in combination, for guided engagement with the cartridge body.

Alignment device 400 as shown in FIG. 9 can be realized for a snap-fit engagement with the cartridge. In comparison with the embodiment of FIG. 7 and FIG. 8, the embodiment of FIG. 9 can allow a slimmer design since alignment device 400 may not surround cartridge body 105. For this embodiment, the axial length of the constricted neck portion of the cartridge body can be exploited for the alignment.

Figure 10:
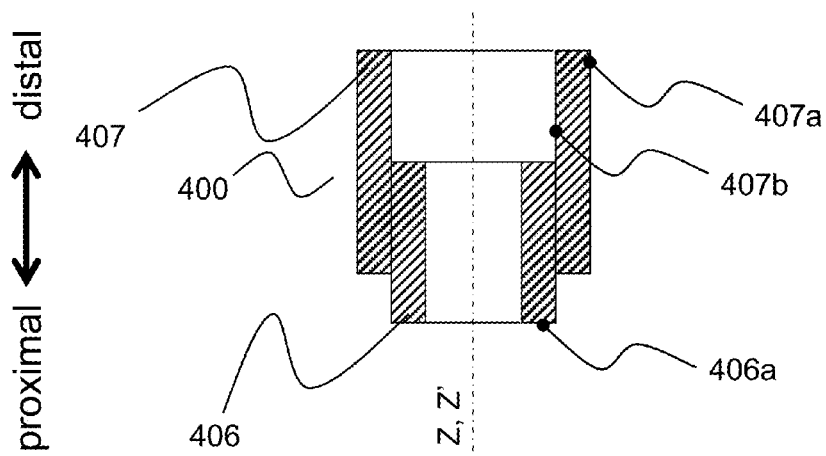
FIG. 10 illustrates schematically a still further embodiment of an alignment device according to an embodiment of the present disclosure.

FIG. 10 shows a further alternative embodiment of alignment device 400. Here, alignment device 400 can be realized by proximal tubular member 406 and distal tubular member 407. The tubular members 406, 407 can be arranged in a telescopic way and can be displaceable with respect to each other along their common longitudinal axis with a guided and smooth fit. The adapter engagement structure can be realized by outer circumferential surface 407*a* of distal tubular member 407. The inner volume of alignment device 400 can receive the constricted neck portion of the cartridge body in the area of proximal tubular member 406 and the cap in the area of distal tubular member 407. Proximal front surface 406*a* of proximal tubular member 406 and inner circumferential surface 407*b* of distal tubular member 407, in combination can serve for guided engagement with the cartridge body. The length of the constricted neck portion of the cartridge body can be exploited for the alignment.

For assembly, alignment device 400 can be first arranged between cartridge and adapter. Then, the adapter can be displaced together with distal member 407 in proximal direction towards the cartridge and proximal tubular member 406 until the adapter cannula can pierce the septum of the cartridge.

The various embodiments of an alignment device 400 may further include anti-rotation ribs as described above in the context of venting devices.

Figure 11A:
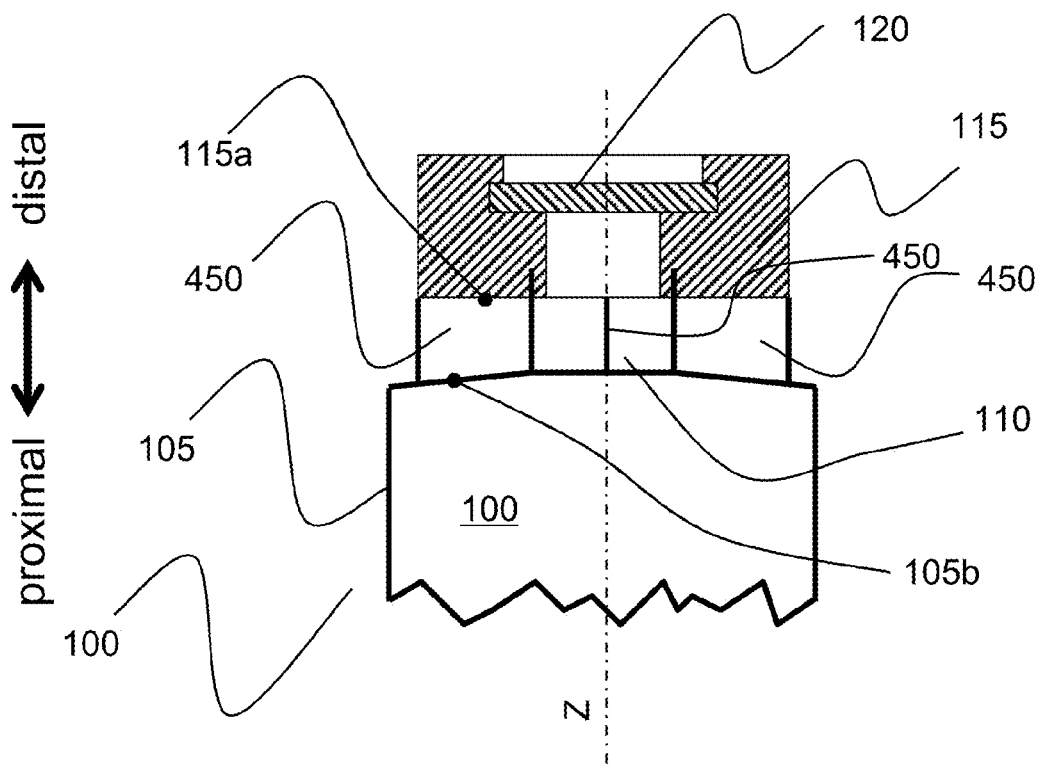
FIGS. 11a-b illustrate schematically a liquid drug cartridge for use in an ambulatory infusion device according to an embodiment of the present disclosure.
Figure 11B:
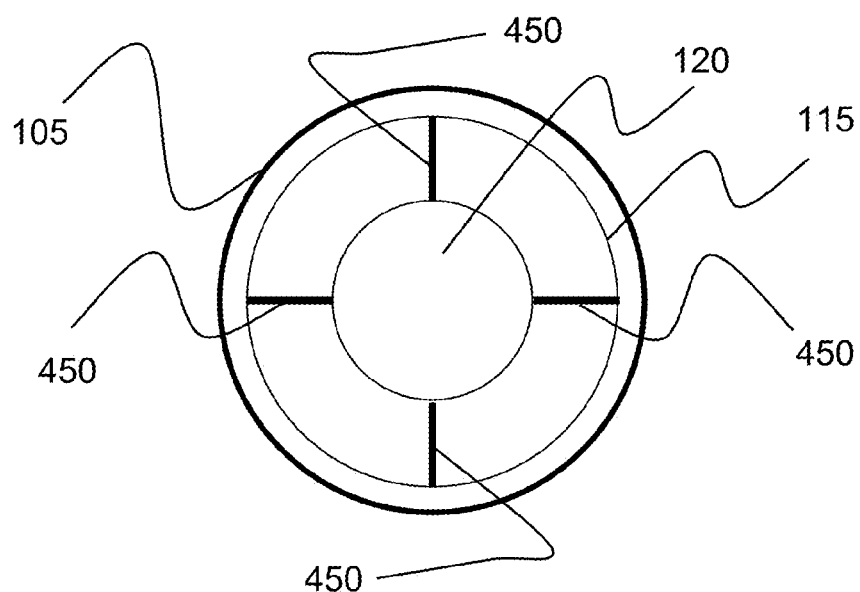

FIGS. 11*a-b* show a liquid drug cartridge for use in an ambulatory infusion. The overall design of cartridge 100 can be similar to the previous embodiments. However, cartridge 100 of this embodiment can comprise a number of alignment members 450 that can be formed integral with cartridge body 105, thus avoiding the need of a dedicated alignment device. Alignment members can be realized by four wings 450 that can be equally distributed about cartridge body 105 and extend along longitudinal cartridge axis Z between distal end 105*b* of cartridge body 105 and proximal front surface 115*a* of cap 115, with the radial dimension corresponding to the cap radius. Cartridge 100 can be designed to couple with an adapter that may be generally designed as in the previous embodiments but can comprise a counter coupling structure that can engage with wings 450 resulting in cartridge 100 guided along the longitudinal cartridge axis Z in a substantially play-free way.

While various aspects of venting devices and of alignment devices are discussed above separately, they may well be combined in a common device. That is, a venting device as discussed above may be designed to fulfill at the same time the function of an alignment device. Vice versa, a venting member, in particular a hydrophobic and gas-permeable membrane, may integrated into an alignment device as discussed, with the body of the alignment device simultaneously serving as carrier member of the venting device.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An alignment device for coupling a liquid drug cartridge having a cartridge body extending along a longitudinal cartridge axis (Z) and, at its distal end, a constricted neck portion and a cap with a piercable septum perpendicular to the cartridge axis (Z) and distal from the neck portion; and an adapter comprising an adapter cannula with a longitudinal cannula axis (Z') to pierce the septum and an infusion device coupler to mechanically couple to and engage with a housing of an ambulatory infusion device, the alignment device comprising:

a proximal cartridge engagement structure designed for axial aligned engagement with a distal end section of the cartridge body;

a distal adapter engagement structure designed for axial aligned engagement with the adapter enabling a coupling of the cartridge with the adapter via the alignment device, wherein the adapter and the cartridge are, during the coupling, aligned by the cartridge engagement structure and the adapter engagement structure respectively relative to each other such that the longitudinal cartridge axis (Z) and the longitudinal cannula axis (Z') form a common longitudinal axis; and wherein the alignment device is distinct from the adapter and the cartridge.

2. The alignment device according to claim 1, wherein the alignment device enables, during the coupling process, an aligned and guided relative displacement of the cartridge and the adapter towards each other along the common longitudinal axis.

3. The alignment device according to claim 1, wherein the cartridge engagement structure surrounds, in the assembled state, a distal section of the cartridge body and/or to project, in the assembled state, from the cap in a proximal direction.

4. The alignment device according to claim 1, wherein the cartridge engagement structure surrounds, in the assembled state, at least one of the neck portion and the cap.

5. The alignment device according to claim 1, wherein the adapter engagement structure has anti-rotation ribs to engage the adapter preventing a relative rotation between the adapter and the alignment device in the engaged state.

6. The alignment device according to claim 1, wherein the alignment device does not radially extend, in the assembled state, beyond the cartridge body.

7. The alignment device according to claim 1, wherein the alignment device has a general tubular shape extending along the common longitudinal axis.

8. The alignment device according to claim 7, wherein the alignment device comprises a proximal tubular member and a distal tubular member, wherein the proximal tubular member forms the cartridge engagement structure and the distal tubular member.

9. The alignment device according to claim 7, further comprises,
   a proximal tubular member, and
   a distal tubular member, wherein when comprising the adapter engagement structure, the proximal tubular member and the distal tubular member are arranged in a telescopic way and are axially guided displaceable with respect to each other along a common tube axis.

10. The alignment device according to claim 1, further comprises,
    a cartridge block designed to prevent further relative displacement between the alignment device and the cartridge upon the cartridge block hitting the cartridge.

11. The alignment device according to claim 1, wherein the cartridge engagement structure and the adapter engagement structure overlap in an axial direction.

12. The alignment device according to claim 1, wherein the adapter engagement structure comprises at least one of a distal section of an outer circumferential surface of the alignment device, an inner circumferential surface of a distal section of the alignment device, and an alignment cavity formed in a distal front surface of the alignment device.

13. The alignment device according to claim 1, further comprising,
    a venting member made from a hydrophobic and gas-permeable material and having an environment coupling surface and an opposed cartridge coupling surface that enables gas transfer and disables liquid transfer across the venting member between the environment coupling surface and the cartridge coupling surface, wherein the alignment device is designed such that, when coupled to the cartridge, the cartridge has a movable wall, wherein the cartridge coupling surface fluidically couples to a no-liquid contacting outer surface of the movable wall, and wherein the environment coupling surface fluidically couples to the environment.

14. A cartridge kit, the cartridge kit comprising:
    an alignment device according to claim 1; and
    a liquid drug cartridge having a cartridge body extending along a longitudinal cartridge axis (Z) and having, at its distal end, a constricted neck portion, wherein the cartridge further comprises a cap with a piercable septum perpendicular to the cartridge axis (Z) and distal from the neck portion, and wherein the cartridge and the alignment device are coupled or designed to couple via the cartridge engagement structure.

15. An adapter kit, the adapter kit comprising:
    an alignment device according to claim 1; and
    an adapter, wherein the adapter comprises an adapter cannula with a longitudinal cannula axis (Z') to pierce a septum of a liquid drug cartridge and an infusion device coupler to mechanically couple to and engage with a housing of the ambulatory infusion device, and wherein the adapter and the alignment device are coupled or designed to couple via the adapter engagement structure.

16. A method for coupling a liquid drug cartridge having a cartridge body extending along a longitudinal cartridge axis (Z) and having, at its distal end, a constricted neck portion, wherein the cartridge further comprises a cap with a piercable septum perpendicular to the cartridge axis (Z) and distal from the neck portion; and an adapter comprising an adapter cannula with a longitudinal cannula axis (Z') to pierce the septum, the method comprising:
    coupling the cartridge and the adapter via an alignment device according to claim 1.

* * * * *